United States Patent
Harrod et al.

(10) Patent No.: US 8,193,398 B2
(45) Date of Patent: Jun. 5, 2012

(54) PROCESSES FOR PRODUCTION AND PURIFICATION OF NORMAL PROPYL BROMIDE

(75) Inventors: William B. Harrod, Minden, LA (US); Bonnie G. McKinnie, Magnolia, AR (US); Alireza M. Dadgar, Magnolia, AR (US); Tyson J. Hall, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 631 days.

(21) Appl. No.: 11/911,792

(22) PCT Filed: Apr. 13, 2006

(86) PCT No.: PCT/US2006/013778
§ 371 (c)(1),
(2), (4) Date: Jul. 10, 2008

(87) PCT Pub. No.: WO2006/113307
PCT Pub. Date: Oct. 26, 2006

(65) Prior Publication Data
US 2008/0318829 A1    Dec. 25, 2008

Related U.S. Application Data

(60) Provisional application No. 60/673,391, filed on Apr. 18, 2005.

(51) Int. Cl.
C07C 17/00    (2006.01)
C11D 17/00    (2006.01)
(52) U.S. Cl. .................................. 570/249; 510/412
(58) Field of Classification Search ............ 510/407
See application file for complete search history.

(56) References Cited

U.S. PATENT DOCUMENTS 2,058,465 A    10/1936    Kharasch
(Continued)

FOREIGN PATENT DOCUMENTS

GB    668159    3/1952
(Continued)

OTHER PUBLICATIONS

CAPLUS Abstract of Smith, et al. "The "peroxide" or "oxygen" effect", Chemistry & Industry, 1937, 10, pp. 833-839. Accession No. 1937:61761 CAPLUS.

(Continued)

*Primary Examiner* — Necholus Ogden, Jr.
(74) *Attorney, Agent, or Firm* — Marcy M. Hoefling

(57) ABSTRACT

A process for oxygen-initiated hydrobromination of propene to form a crude reaction mixture of 95 GC area % n-propyl bromide. The process includes feeding an oxygen-containing gas, propene and hydrogen bromide into a liquid phase mixture comprised of n-propyl bromide and hydrogen bromide. At least the oxygen-containing gas and the propene of the feed are fed subsurface to the liquid phase mixture and either (a) the oxygen-containing gas and the propene do not come together in the absence of hydrogen bromide or (b) the oxygen-containing gas and the propene come together only in a propene:oxygen molar ratio in the range of 145:1 to 180:1. Purification processes provide a propyl bromide product containing at least 99.7 GC area % n-propyl bromide. Also provided is a novel composition of enhanced thermal stability which comprises a mixture of n-propyl bromide and isopropyl bromide. The mixture has an n-propyl bromide content of at least 99.7 GC area %, and an isopropyl bromide content of no more than 0.05 GC area %. The mixture, if subjected to storage in a closed chemically inert container at 60° C. for at least 480 hours, has an APHA color of 10 or less while the mixture is devoid of any added stabilizer component.

20 Claims, 5 Drawing Sheets

U.S. PATENT DOCUMENTS

| | | | |
|---|---|---|---|
| 2,058,466 A | | 10/1936 | Kharasch |
| 2,299,411 A | * | 10/1942 | Rust et al. .................... 570/249 |
| 2,307,552 A | | 1/1943 | Vaughan et al. |
| 2,672,439 A | * | 3/1954 | den Hertog et al. .......... 204/169 |
| 2,790,013 A | | 4/1957 | Barnes et al. |
| 3,108,141 A | | 10/1963 | Gasson et al. |
| 3,321,538 A | | 5/1967 | Theile et al. |
| 3,679,759 A | | 7/1972 | Schmerling |
| 3,683,037 A | | 8/1972 | Hay et al. |
| 3,699,179 A | | 10/1972 | Boyle et al. |
| 5,690,862 A | | 11/1997 | Moore, Jr. et al. |
| 5,707,954 A | | 1/1998 | Lee |
| 5,773,672 A | * | 6/1998 | Harrod et al. .................. 570/249 |
| 5,792,277 A | | 8/1998 | Shubkin et al. |
| 5,858,953 A | | 1/1999 | Aman et al. |
| 2002/0151447 A1 | | 10/2002 | Henry |

FOREIGN PATENT DOCUMENTS

| | | |
|---|---|---|
| GB | 841745 | 7/1960 |
| GB | 843234 | 8/1960 |
| GB | 867549 | 5/1961 |
| GB | 927114 | 5/1963 |
| GB | 2024242 A | 1/1980 |
| JP | 1292095 | 11/1989 |
| JP | 6220494 | 8/1994 |
| JP | 7150197 | 6/1995 |
| JP | 8067643 | 3/1996 |
| JP | 8337795 | 12/1996 |
| JP | 9302389 | 11/1997 |
| JP | 10046197 | 2/1998 |
| JP | 11246898 | 9/1999 |
| JP | 11293287 | 10/1999 |
| SK | 81794 | 2/1996 |
| WO | 9850517 A1 | 11/1998 |
| WO | 2006113307 A1 | 10/2006 |

OTHER PUBLICATIONS

Author unknown, "N-Propyl Bromide", Sinobrom Limited Website, <http://www.sinobrom.co.uk/se_bromine_g/n-propyl_bromide.asp> (Visited Jan. 30, 2004), 2 pages.

Brouwer, et al., "On the Addition of Gaseous Hydrogen Chloride and Hydrogen Bromide to Propene Under the Influence of Catalysts", Recueil Des Travaux Chimiques Des Pays-Bas, vol. 53, 1954, pp. 1001-1010.

Hertog, et al., "Addition Reactions of Alkenes in Silent Electrical Discharges", Proceedings of the Koninklijke Nederlandse Akademie Van Wetenschappen, vol. 54, 1951, pp. 379-386.

Kharasch, et al., "The Peroxide Effect in the Addition of Reagents to Unsaturated Compounds", J. Amer. Chem. Soc., vol. 56, Jun. 1934, p. 1425.

Kharasch, et al., "The Peroxide Effect in the Addition of Reagents to Unsaturated Compounds. III. The Addition of Hydrogen Bromide to Propylene," J. Amer. Chem. Soc., 1933, vol. 55, pp. 2531-2533.

Mayo, et al., "The Addition of Hydrogen Bromide to Propylene", Journal of Am. Chem. Soc., 1947, vol. 69, pp. 1348-1351.

Mayo, et al., "The Peroxide Effect in the Addition of Reagents to Unsaturated Compounds and in Rearrangement Reactions", Chem. Rev., 1940, vol. 27, pp. 351-412.

Rust, et al., "The Olefin-Oxygen-Hydrogen Bromide Photo-Reaction", J. Org. Chem., 1942, vol. 7, pp. 491-496.

Vaughan, et al., "The Photo-Addition of Hydrogen Bromide to Olefinic Bonds", J. of Org. Chem., 1942, vol. 7, pp. 477-490.

* cited by examiner

PROCESSES FOR PRODUCTION AND PURIFICATION OF NORMAL PROPYL BROMIDE

REFERENCE TO RELATED APPLICATIONS

This application is the National Stage of International Patent Application PCT/US2006/13778, filed on Apr. 13, 2006, which application claims priority from U.S. Application No. 60/673,391, filed Apr. 18, 2005, the disclosures of which are incorporated herein by reference.

TECHNICAL FIELD

This invention related to improved processes for production and purification of normal propyl bromide (a.k.a. 1-bromopropane and n-propyl bromide). For convenience, normal propyl bromide will be hereinafter referred to as NPB.

BACKGROUND

NPB presents an ecologically friendly alternative to 1,1,2-trichloroethane (TCE) for uses such as a cold cleaning solvent. TCE has been identified as having characteristics that are reported to link it to depletion of the earth's ozone layer, thus creating a need for a replacement which will not harm the environment.

Methods of synthesis of NPB are known. Kharasch et al., J. Am. Chem. Soc. 1933, 55, 2532-3, describes addition of hydrogen bromide to propene in the presence of peroxides such as benzoyl peroxide or ascaridole to form NPB. See also Kharasch U.S. Pat. No. 2,058,466. Vaughan et al., J. Org. Chem. 1942, 7, 477-90, describes synthesis, inter alia, of NPB by photohydrobromination of propene in liquid phase. See also Vaughan et al. U.S. Pat. No. 2,307,552. Formation of NPB from vapor phase reaction of hydrogen bromide and propene in the presence of activated carbon catalyst is described in U.S. Pat. No. 2,790,013 to Barnes. U.S. Pat. No. 3,679,759 to Schmerling reports preparation of NPB from concentrated hydrobromic acid and propene at 225° C. and 30-74 atmospheres pressure. British 668,159 reports formation of NPB by passing a mixture of 2 parts by volume of propene and 3 parts of hydrogen bromide gas at the rate of 300 cc per minute into a Siemens-type glass ozonizer.

Some of methods of producing NPB include commercial production by substitution reactions of 1-propanol, by hydrobromination of propene using ozonide catalysts, and by free radical hydrobromination of propene. The latter technology co-produces the secondary bromide isomer, known as isopropyl bromide (IPB). This results in a crude reaction mixture of NPB and IPB, the latter being an undesirable isomer. In certain applications, purities of NPB in excess of 98% are needed which makes it highly desirable to remove IPB from the mixture.

When crude propyl bromide reaction mixtures, formed from a synthesis process employing hydrobromination of propene by hydrogen bromide, are washed with a basic solution to neutralize any excess hydrogen bromide, emulsion problems can result. Such problems are manifested by failure of the alkaline-treated mixture to resolve into two distinct phases, which resolution is necessary for efficient and economical post-synthesis handling of such reaction mixtures.

Therefore a need exists for an NPB synthesis process which provides high yields of NPB in a highly pure state and on an industrial scale, while maintaining safe process conditions and while eliminating undesirable isomers, as in the case of IPB.

A need also exists for a purification process which provides quick and clean phase-cut technology to allow distinct organic/aqueous phase separation for any process wash steps to be employed in an efficient and economical manner. Additionally, a need exists for an NPB composition that maintains its purity and color under typical storage conditions, without the need for additives or stabilizers.

This invention is deemed to enable fulfillment of the foregoing needs and others by the use of the methods and compositions of this invention.

SUMMARY DISCLOSURE OF THE INVENTION

This invention provides at least (I) a novel synthesis process which provides high yields of NPB by oxygen-initiated hydrobromination of propene, (II) a novel process of separation of NPB from a crude mixture comprising NPB and IPB, (III) a novel process for forming a crude reaction mixture comprising NPB and IPB by oxygen-initiated hydrobromination of propene and purifying the crude reaction mixture to yield highly pure NPB, and (IV) a novel composition of enhanced thermal stability, devoid of any added stabilizer, comprising a mixture of NPB and IPB where the NPB content is high, the undesirable IPB content is very low and the mixture has a very low APHA color after being subjected to extended storage at 60° C.

I. Oxygen-Initiated Hydrobromination of Propene

As used herein the term "oxygen-containing gas" includes any amount of free oxygen which includes oxygen sufficient to initiate the reaction. Such gases include pure oxygen gas itself, and mixtures of oxygen with other gases (e.g., air, mixtures of oxygen or air and one or more inert gases and air enriched in oxygen). References to oxygen-containing gas and oxygen are understood to refer to oxygen as molecular oxygen ($O_2$).

This invention provides a novel synthesis process which allows high yields of NPB by oxygen-initiated hydrobromination of propene. Although oxygen can be provided in its pure form, diluted mixtures of oxygen in other gases are preferred due to safety concerns. It is particularly preferred that the oxygen be supplied in an oxygen-containing gas such as air. Safety considerations, especially avoidance of the flammable and/or explosivity range of propene/oxygen-containing gas mixtures, are provided for in both the processing and the purification aspects of the invention. An advantage of this oxygen-initiated approach is that it avoids certain by-products, such as carbonates, generated by other hydrobromination reaction processes.

In accordance with a preferred embodiment of this invention, NPB is produced by a process which comprises initiating feeds of (A) an oxygen-containing gas as a reaction initiator, (B) propene and (C) hydrogen bromide (HBr) into a liquid phase mixture comprised of NPB and HBr in an amount in the range of 1.1 wt. % to 1.5 wt. %. At least the oxygen-containing gas and the propene of the feed are fed subsurface to the liquid phase mixture. Propene is preferably fed as a gas, as is HBr. Although HBr can be stored as a liquid under pressurized conditions, it is fed as a gas. Either (a) the oxygen-containing gas and the propene do not come together in the absence of hydrogen bromide or (b) the oxygen-containing gas and the propene come together in the absence of HBr only in a propene to oxygen molar ratio in the range of about 145 to 180 moles of propene for one mole of oxygen. A ratio in the range of about 150 to 170 moles of propene to one mole of oxygen is preferred, and a ratio of about 163 moles of propene to one mole of oxygen is particularly preferred. These ratios are derived from calculations involving application of the ideal gas laws under conditions of standard temperature and pressure, and assume a molar content of 21% oxygen in air. These measurements, made under actual service conditions, may depart to a small extent from these ratios and yet remain within the scope of this invention. The ratios of propene to oxygen are designed to meet the requirements of safe handling of these components within the limits of the mechanical equipment available. The process of preparing NPB forms a crude reaction mixture which is conducted in reaction equipment having contacting surfaces essentially devoid of reaction inhibitors and contains at least 95 GC area % NPB.

Without being bound by theory, it is conjectured that only trace amounts of oxygen, perhaps in the ppm range, may be necessary to initiate the hydrobromination processes of this invention. The processes of this invention are conducted under reaction conditions effective to produce NPB as the principal component of the crude reaction mixture formed in the reaction. In an embodiment of the invention in which propene and oxygen-containing gas are pre-mixed and fed sub-surface to the mixture, excellent results are achieved by proportioning the propene and oxygen such that there is a molar ratio of propene relative to oxygen which ensures that the ratio of propene to oxygen is not allowed to enter the flamability range for this mixture. In another embodiment of the invention, the oxygen-containing gas and the propene do not come into contact in the absence of hydrogen bromide.

Separate feeds of oxygen-containing gas, propene as a gas and hydrogen bromide as a gas can be introduced either sequentially or concurrently into a liquid heel comprised of a liquid phase mixture comprised of NPB and HBr. The liquid phase mixture preferably contains HBr in a range of 1.1 wt. % to 1.5 wt. % based on the weight of the liquid phase mixture which represents an excess of the stoichiometric amount of HBr necessary for reaction with propene when measured at atomospheric pressure. More preferably the amount of HBr in the liquid phase mixture is in the range of 1.2 to 1.3 wt. %. Solubility of HBr in liquid NPB is such that this concentration range of HBr in NBP represents a liquid phase mixture at atomospheric pressure which is substantially saturated with HBr.

When feed of propene is begun, the molar ratio of HBR to propene in the liquid phase mixture is preferably about 1.0:1.0. The molar ratio of HBr to propene marginally increases under optimum pressurized reaction conditions to about 1.1:1.0. Surprisingly high selectivity for formation of NPB in the crude reaction mixture can be achieved under these conditions. It is believed that high conversions result at least in part from the selectivity of the primary isomer of propyl bromide in the free radical mechanism of the oxygen-initiated hydrobromination in an reaction environment devoid of reaction inhibitors, together with maintaining an excess of HBr in order to drive the reaction to completion. In fact it is possible to obtain as great as at least 95 GC area % NPB in the crude reaction mixture. Preferably the crude reaction mixture contains at least 96 GC area % NPB and more preferably at least 97.8 GC area % NPB.

II. Separation of NPB from a Crude Mixture of NPB and IPB

Another preferred embodiment of the present invention provides a process for separating NPB from a crude mixture comprising NPB and IPB. The process comprises first washing at least a portion of the crude mixture one or more times with a wash comprising an aqueous solution or aqueous suspension of at least one alkali metal hydroxide. It has been found that using a wash of an aqueous solution of alkali metal hydroxide having a concentration in the range of 3 to 5 moles per liter causes formation of an aqueous phase and an organic phase without encountering the problem of emulsion formation. After separating the phases by conventional means, at least a portion of the organic phase can optionally be washed with water to form an organic phase and an aqueous phase. Whether or not the optional water wash is performed, the phases are separated and one or more distillations is carried out on at least a portion of the organic phase so separated, to form a highly pure propyl bromide product. The propyl bromide product preferably is comprised of at least 99.7 GC area % NPB and no more than 0.05 GC area % IPB. More preferably, the propyl bromide product comprises at least 99.8 GC area % NPB and no more than 0.03 GC area % IPB.

III. Combined Process of Oxygen-initiated Hydrobromination of Propene and Purification of the Crude Reaction Mixture In a further embodiment of the invention the conditions of the processes of (I) and (II) as detailed above apply so that a novel, highly effective combination synthesis and purification process is provided to form highly pure propyl bromide product. Improved ease of purification is accomplished in a preferred embodiment of the invention by using a non-conventional concentration of an aqueous alkaline solution during the purification process. An embodiment of this invention provides a process which comprises (1) initiating feeds of (A) an oxygen-containing gas, (B) propene and (C) hydrogen bromide into a liquid phase mixture comprised of NPB and hydrogen bromide in an amount in the range of 1.1 wt. % to 1.5 wt. % based on the weight of the liquid phase mixture. At least the oxygen-containing gas and the propene of the feed are fed subsurface to the liquid phase mixture. Either (a) the oxygen-containing gas and the propene do not come together in the absence of hydrogen bromide or (b) the oxygen-containing gas and the propene come together in the absence of HBr only in a propene:oxygen molar ratio in the range of 145:1 to 180:1, to form a crude reaction mixture in reaction equipment having contacting surfaces essentially devoid of reaction inhibitors. The crude reaction mixture contains at least 95 GC area % NPB. The reaction inhibitors which are particularly to be avoided are those containing the metals iron and/or titanium as well as compounds containing these metals.

The process further comprises: (2) purifying the crude reaction mixture by: (1) washing at least a portion of the crude reaction mixture one or more times with a wash comprising an aqueous solution of an alkali metal hydroxide having a molar concentration of 3 to 5 moles per liter to form an aqueous phase and an organic phase and then separating the phases thus formed; (II) optionally, washing at least a portion of the organic phase from (I) with water to form an aqueous phase and an organic phase and then separating the phases thus formed; and (III) either (i) when (I) is conducted and (II) is not conducted, distilling at least a portion of the organic phase from (I) one or more times; or (ii) when (I) and (II) are conducted, distilling at least a portion of the organic phase from (II) one or more times. A propyl bromide product is formed comprising at least 99.7 GC area % NPB. NPB content of at least 99.8 GC area % can be achieved using preferred embodiments of this invention and even more preferable amounts of NPB of at least 99.9 GC area % are possible. Also attainable using preferred embodiments of this invention are amounts of IPB of no more than 0.05 GC area %, more preferably no more than 0.03 GC area % and even more preferably IPB amounts of no more than only 0.02 GC area %.

In a particularly preferred embodiment of the invention, the propyl bromide product comprises at least 99.8 GC area % NPB, up to 0.03 GC area % IPB and exhibits an APHA color of 10 or less.

IV. Mixture of NPB and IPB Having Enhanced Thermal Stability and being Devoid of any Added Stabilizers Another embodiment of this invention provides a novel composition comprising a mixture of NPB and IPB having excellent thermal stability. A particularly preferred embodiment of the invention provides a composition of enhanced thermal stability which comprises a mixture of NPB and IPB, wherein the mixture has an NPB content of at least 99.7 GC area % and an IPB content of no more than 0.05 GC area %, wherein the mixture, if subjected to storage in a closed chemically inert container at 60° C. for at least 480 hours, has an APHA color of 10 or less and wherein the mixture is devoid of any added stabilizer component.

Since IPB has been reported to possibly raise undesirable health issues, the compositions of this invention provide a highly desirable mixture of NPB and IPB having no more than 0.05 GC area % of IPB. In particular a highly purified NPB mixture having no more than 0.03 GC area % of IPB is provided. Also provided is a composition having a more particularly preferred IPB content no more than 0.02 GC area %. Surprisingly, the product mixture thus provided is novel in its ability to maintain excellent color and high purity (low IPB content) even after storage at temperatures of about 60° C. for at least 720 hours.

The above and other embodiments of this invention will be apparent from the ensuing description and appended claims.

BRIEF DESCRIPTION OF DRAWINGS

In each of the above figures, like numerals are used to refer to like or functionally like parts among the several figures.

DETAILED DISCLOSURE OF THE INVENTION

Figure 1:
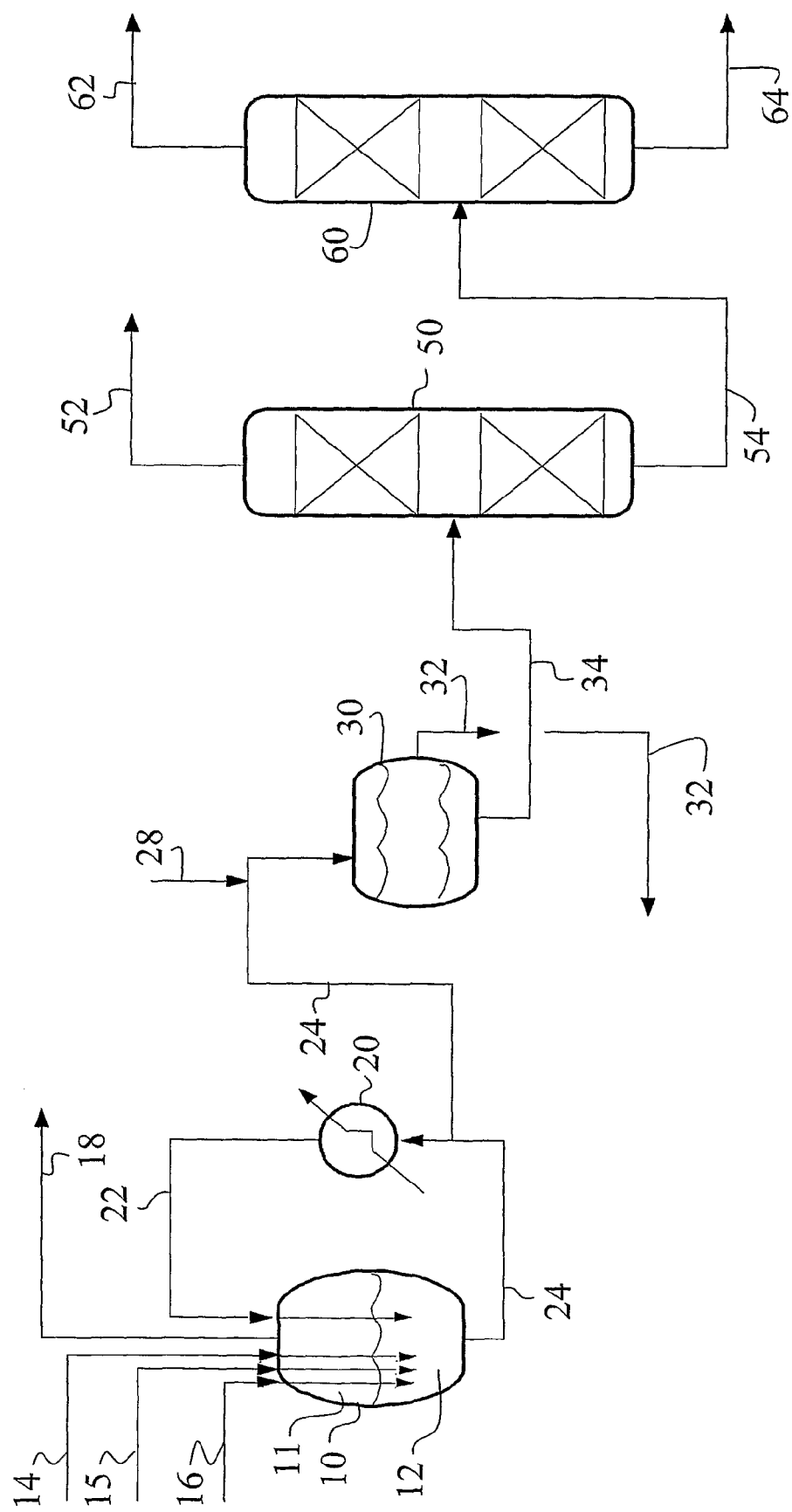
FIG. 1 is a schematic flow diagram for producing and purifying NPB.

The hydrobromination processes of I and III as outlined above are conducted in by feeding gaseous HBr, gaseous propene and oxygen-containing gas into a liquid phase mixture comprised of liquid NPB and solubilized HBr. In conducting the oxygen-initiated hydrobromination process of this invention, it is preferred that gaseous hydrogen bromide, gaseous propene and oxygen-containing gas are fed separately, although it is possible that these components can be fed in combination. At least the gaseous propene and oxygen-containing gas are fed subsurface to the liquid phase mixture of NPB and HBr. While gaseous HBr can be fed to the reaction vessel either sub-surface or super-surface of the liquid phase mixture, sub-surface addition is preferred for large-scale operations. In an alternative embodiment of hydrobromination processes, gaseous propene and oxygen-containing gas are pre-mixed before being fed subsurface to the liquid phase mixture, with HBr being fed super-surface. The ratio of moles of propene to 1 mole of oxygen (as molecular oxygen) is in the range of 145:1 to 180:1 and more preferably in a molar ratio in the range of 155:1 to 165:1 moles of propene per mole of oxygen, in order to keep the propene to oxygen molar ratios outside the explosive range of mixtures of propene and oxygen. A particularly preferred ration of propene to oxygen is about 163:1. Despite the fact that propene is a highly flammable, gaseous material, and that there is a potential for explosive combustion with oxygen in oxygen-containing gas, the process of this invention can be efficiently and safely operated.

The primary safety concerns of potential flammability/explosivity are associated with pre-mixture of oxygen-containing gas with propane, and are overcome by maintaining the proper molar ratios of propene to oxygen. The flammability limits are listed in the literature as being 2.4-10.3% propene in air, by volume (Merck Index, 12 Ed. p. 1348, Merck and Co., Whitehouse Station, N.J. (1996)). Safety concerns guide the choice of proportions and rate of feed of the components, which are designed to maintain excess propene above the flammability range.

Maintaining molar ratios of propene to oxygen which are well outside the flammability/explosivity ranges for these two components, as previously described, are of primary importance when the two are pre-mixed as in a preferred embodiment of the invention. Molar ratios in the range of 145:1 to 180:1 for propene:oxygen are also maintained when propene and oxygen-containing gas are fed separately, as in another preferred embodiment of the invention.

The initial liquid phase mixture is formed by feeding gaseous HBr into a reaction vessel containing liquid NPB as a non-polar solvent to establish an amount of HBr in liquid phase mixture the range of 1.1 wt. % to 1.5 wt. % based on the weight of the liquid phase mixture. Preferably the amount of HBr in the liquid phase mixture initially is in the range of 1.2 wt. % to 1.3 wt. %. This ensures about a 1 to 3 wt. % excess of HBr relative to NPB. HBr is maintained at a stoichiometric excess, when measured at atmospheric pressure, relative to propene present in the liquid phase mixture during reaction by feeding gaseous propene and gaseous hydrogen bromide in approximately equimolar amounts.

Favorable reaction conditions include elevated pressures in the range of 20 to 165 psi (137.9–1137.6 kPa) and more preferably in the range of 20 to 30 psi (137.9–206.8 kPa) for laboratory equipment. A preferred pressure range for commercial operations is a range of 20 to 165 psi (137.9–1137.6 kPa), preferably in the range of 20 to 75 psi (137.9-517.1 kPa) and more preferably pressures in the range of 45 to 75 psi (310.3–517.1 kPa).

A further advantage of the present invention is that the hydrobromination reaction takes place at moderate temperatures in the range of 5° C. to 45° C. for laboratory equipment and more preferably in the range of 20° C. to 45° C. Preferred temperatures for larger scale commercial operations are in the range of 0° C. to 70° C., and more preferably temperatures in the range of 45° C. to 55° C. Conversions as high as about 99.9 mole percent or more, based on HBr, can be achieved.

The hydrobromination process is also highly advantageous in that it utilizes two reactants (HBr and propene) which in large measure are produced as co-products of other industrial processes, and thus the process conserves resources which might otherwise be wasted, while at the same time converting them with high (but not necessarily complete) specificity to a highly useful industrial product, NPB. Since the oxygen in air is preferred as the reaction initiator, the processes of the present invention are more economical than, for instance, the ozonide process which requires special catalyst production. Typically at least 95 GC area % of the crude product formed is the primary isomer with the balance, if any, being almost entirely the secondary isomer, with possible small amounts of one or more impurities, such as a dibromopropane isomer. Because the process is so highly efficient, the proportion of co-products requiring disposal are minimal, and thus the process is an environmentally wholesome operation.

The oxygen-containing gas serves as a reaction initiator for the hydrobromination processes and can be introduced combined with the propene or separately, subsurface to the liquid phase mixture which comprises NPB and hydrogen bromide. The oxygen-containing gas can be introduced in the form of an admixture where the oxygen is mixed with a carrier gas such as the oxygen which is normally found in air. The carrier gas/oxygen admixture can also comprise a carrier gas such as an inert gas. Such inert gases may include, for example the noble gases, helium, argon and neon. The carrier gas can also comprise other noncombustible gases such as nitrogen.

For the separation process of II and purification process of III, preferably the wash comprising an aqueous solution or aqueous suspension of alkali metal hydroxide has a molar concentration in the range of 3.2 to 4.5 moles per liter. Alkali metal hydroxides utilized in the processes of the invention can be, for example, potassium hydroxide, lithium hydroxide, quarternary ammonium hydroxide, or sodium hydroxide, with sodium hydroxide most preferred.

Another embodiment of this invention provides a process for effectively separating NPB from a crude mixture, which crude mixture may be formed by a synthesis process in which HBr is reacted with a propene, as in the presently claimed invention. The crude mixture comprises NPB and IPB, dibromopropane and small amounts of other impurities.

Without being bound by theory, it is believed that high NPB content formed in the hydrobromination reaction is made possible, at least in part, by having a crude reaction mixture which is conducted in reaction equipment which is constructed and configured to avoid any contact between the crude reaction mixture and structures or surfaces made with reaction inhibitors.

Reaction inhibitors include any species of contaminant that interferes with the formation of the primary isomer of propyl bromide, such as those which would promote formation of the secondary isomer of propyl bromide or otherwise cause unacceptably low amounts of NPB in the crude reaction mixture. Recognized reaction inhibitors include, but are not limited to, certain metals and metal-containing compounds such at iron and titanium. Particular car is exercised to avoid iron and titanium contamination such as by providing an inert lining for the reaction vessel. In addition to contributing to unacceptably low amounts of NPB in the crude reaction mixture, iron and titanium are believed to contribute to production of color bodies that have a negative impact on color values of the final product. Therefore in instances where product of minimal color and high purity are desired it is preferred to use a glass-lined or otherwise inert reaction vessel so as to minimize the presence of iron, titanium or the like.

After formation of a crude reaction mixture, it is optional but preferred to first wash the crude reaction mixture with water to solubilize excess hydrogen bromide and provide for its separation and removal in an aqueous phase. Removal of a large proportion of entrained hydrogen bromide at this time permits more efficient neutralization of the hydrogen bromide remaining in the organic phase in a subsequent step. Phase separation performed on the water-washed crude product mixture yields an organic and an aqueous phase. The organic phase is then subjected to subsequent steps in the separation procedure.

At least a portion of the crude mixture is washed one or more times with an aqueous mixture or aqueous suspension of an alkali metal hydroxide. Aqueous sodium hydroxide having a concentration in the range of about 3.2-4.5 moles per liter is preferred. It was found that by using a concentration of aqueous sodium hydroxide of about 4 M (4 moles/liter) (12.5 wt. %), a phase separation problem can be avoided. A phase separation problem was detected when using a more concentrated 8 M (8 moles/liter) (25 wt %) NaOH. Specifically, phase cut problems were seen when using 481.6 g of crude propyl bromide and 102.4 g of aqueous 25 wt. % NaOH. An initial exotherm to 44° C. was seen, and no phase separation was observed after 20 minutes. In sharp contrast, when 180 g of aqueous 12 wt. % NaOH, prediluted from aqueous 25 wt. % NaOH, was mixed with 471.76 g crude propyl bromide, the phase separation occurred with 5-10 seconds. The phase cut was clean with an exotherm to about 40° C.

The organic and aqueous phases formed by the wash with aqueous base are separated by conventional means. Optionally, at least a portion of the organic phase of the wash with aqueous alkali metal hydroxide or aqueous suspension of alkali metal hydroxide is washed with water to form an aqueous phase and an organic phase. Although optional, this additional water wash is desirable to prevent the propyl bromide product from reacting with hydroxide ions in an elimination reaction, which could produce flammable propene, water and alkali metal bromide (solid).

At least a portion of the organic layer, either separated from the alkali metal hydroxide wash or from the optional water wash step conducted after the basic wash, is subjected to at least one distillation to obtain a very pure propyl bromide product. The propyl bromide product is comprised of at least 99.80 GC area % NPB and no more than 0.05 GC area % IPB. The IPB content which results from conducting the process of this invention is more preferably no more than about 0.03 GC area %.

One preferred distillation is best carried out, on a laboratory scale, in an Oldershaw distillation column having at least 20 trays where the bottoms product comprises a very high content of the desirable NPB. An optional, though preferable, second flash distillation is also carried out in laboratory-scale equipment on the bottoms product of the first distillation to provide the very high purity NPB with low APHA color and good stability at the specified temperature.

In a preferred embodiment of the invention, at least a portion of the organic phase formed by either the basic wash step or the water wash step is contacted with a drying agent. After the organic phase contacts the drying agent, the drying agent is separated from the dried organic phase, and then the dried organic phase is distilled one or more times. The drying agent used can be a typical material suitable of this purpose, preferably either calcium sulfate or calcium chloride.

Novel compositions are provided in an embodiment of this invention which comprises a mixture of NPB and IPB. The mixture has an NPB content of at least 99.7 GC area % and an IPB content of no more than 0.05 GC area %. The mixture, if subjected to storage in a closed chemically inert container at 60° C. for at least 480 hours, has an APHA color of 10 or less. The composition is devoid of any added stabilizer component. A more preferred embodiment of the invention has a IPB content of no more than 0.03 GC area %. In another embodiment of the invention, good APHA color values and low IPB content were maintained after storage of the unstabilized mixture at 60° C. for at least 720 hours.

Turning now to the figures, FIG. 1 represents a process scheme of an embodiment of the invention for forming the crude reaction mixture and then separating and purifying the components of the crude reaction mixture to yield a mixture of isomers of propyl bromide having a very high NPB content. In the flow diagram depicted, a pressure-safe reactor vessel 10 contains liquid phase mixture 12 of hydrogen bromide and NPB and head space 11. Hydrogen bromide feed line 14, propene feed line 15 and feed line 16 for oxygen-containing gas deliver each of these components sub-surface to liquid mixture 12. Pumps (not shown) provide motive force for these feeds. Reactor 10 is provided with a pump-around loop composed of exit line 24, cooler 20 and return line 22. A portion of a crude reaction mixture, comprised primarily of HBr, NPB, IPB, dibromopropane, water formed during the hydrobromination reaction, and small amounts of other reaction side products from the liquid phase reaction mixture of reactor 10 is circulated via line 24, passes through cooler 20 and back into reaction vessel 10 through return line 22. Cooler 20 helps maintain desired reaction temperatures in the range of about 45 to 55° C. Reactor vent line 18 allows desired pressure ranges to be maintained by allowing periodic venting of reaction component vapors, thus permitting reaction pressure in the range of about 45 to 75 psi (310.3-517.1% kPa) to be maintained. In a preferred embodiment of the invention substantially all propene reacts with HBr, since HBr is supplied in slight excess initially. Subsequently, a molar ratio of moles of HBr fed to moles of propene fed are about 1:1. Any unreacted propene, if it exists, exits by way of reactor vent line 18, as does any propane which may be present as an impurity in the propene feed. A portion of the crude reaction mixture passes though line 24 to phase separation vessel 30.

Still referring to FIG. 1, aqueous alkali metal hydroxide solution addition line 28 is shown where aqueous sodium hydroxide (3-5 molar) is added before the crude product passes into phase separation vessel 30 through line 24. A phase cut in vessel 30 allows an aqueous phase to be drawn off through line 32 and for the organic phase to proceed to distillation via line 34.

Although not shown, it is to be understood that an optional addition of water can be made to the crude product by inserting a phase cut operation between the reaction vessel and the point of addition of sodium hydroxide. The purpose and benefit of such optional operation steps are to wash out hydrogen bromide which is entrained with the crude reaction mixture. The hydrogen bromide separates with an aqueous phase and the organic phase continues through the depicted scheme to be treated with aqueous sodium hydroxide solution. This decrease in hydrogen bromide in the crude reaction mixture will favorably impact the amount of aqueous alkali metal hydroxide solution needed to be added through line 28 so as to result in cost savings.

Returning now to FIG. 1, an organic phase containing NPB and small amounts of IPB and dibromopropane are transported from phase separation vessel 30 by way of line 34 to a distillation column 50 where IPB and any remaining water are carried overhead in line 52 and NPB and dibromopropane are carried through line 54 to distillation column 60. A second distillation operation in column 60 causes separation of an NPB final product though overhead line 62 and dibromopropane though bottoms line 64.

The distillation columns employed in the preferred embodiments of this invention are constructed with interior surfaces which are chemically inert. Suitable construction materials for these distillation columns include, for example, stainless steel and carbon steel. If carbon steel is used, however, it is highly desirable to provide a chemically inert lining such as glass, TEFLON® polymer, or KYNAR® polymer. A preferred embodiment of the invention uses a glass-lined carbon steel configuration.

The interior design of these distillation columns can be of any type known to provide the desired split of components. The distillation columns can be fitted with interior trays of various shapes and numbers or be packed with varying materials. A preferred interior design for the distillation columns is to have the column packed with one or a combination of inert packing materials, such as structured packing (stacked disks of varying materials and configurations) or random "dumped" packing (inert particles of varying shapes and sizes are loaded into the column in a random way). Preferred types of "dumped" packing include particles constructed of glass, inert metal, or ceramic material which may take shapes such as beads, shards, rings, protruded metal, and saddles. Particularly preferred are ceramic beads which are non-reactive in an environment which has the possibility of HBr presence.

As may be seen in the previous discussion, distillation column configuration is highly dependent on the particular application involved. Many combinations of size, materials of construction and run parameters are possible, as long as the choices provide acceptable ranges of purity of the final product in an economically feasible manner.

Temperature profiles of each distillation column are also to be understood to be dictated by the boiling points of the particular distillation factions which are to be carried in the overhead or bottom streams for each respective column. These boiling points are readily determinable from the literature and will not be detailed further.

Figure 2:
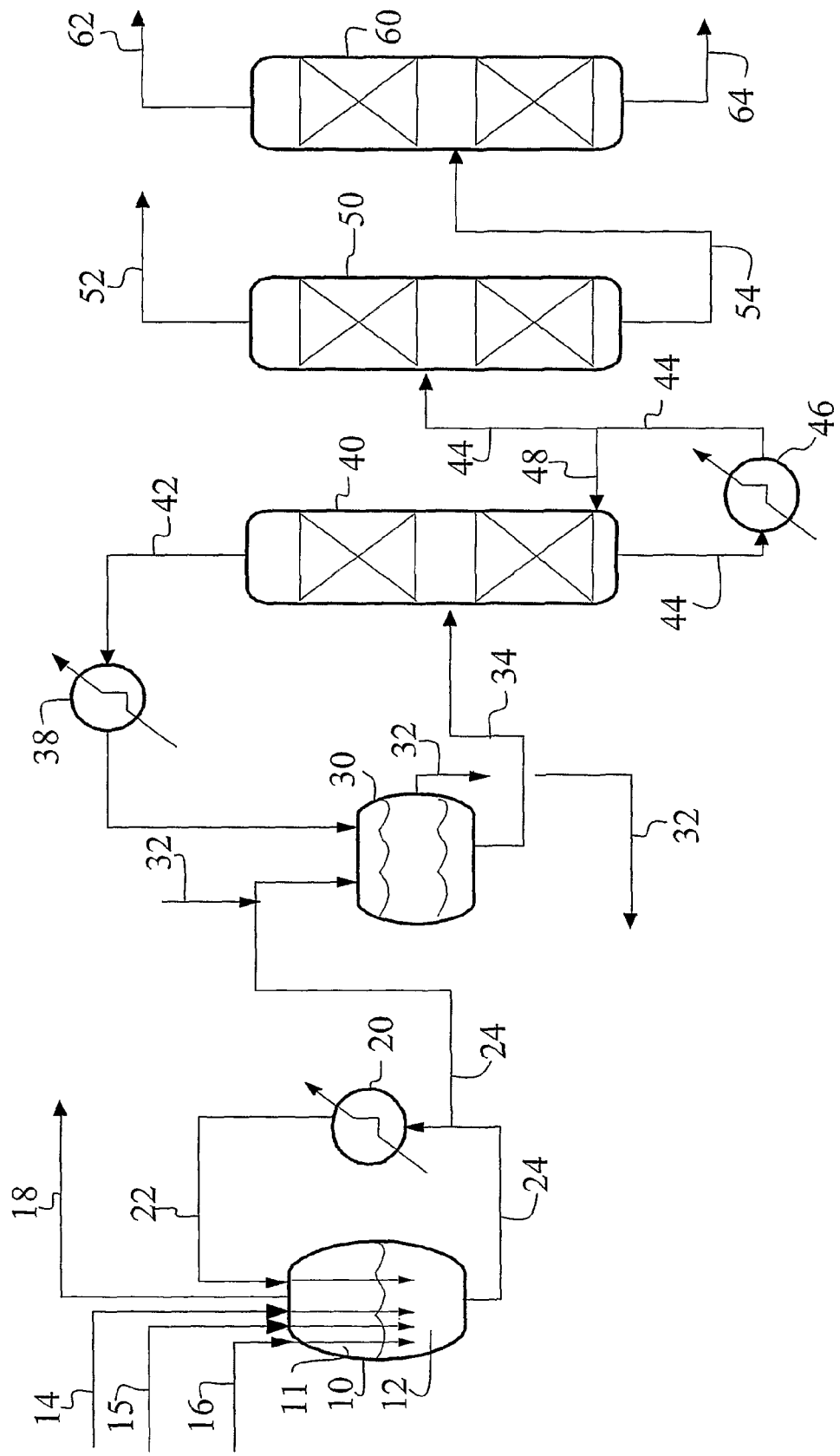
FIG. 2 is the schematic flow diagram of FIG. 1 with an alternative scheme involving an additional distillation column.

The scheme of FIG. 2 is essentially the same as FIG. 1 with the addition of an optional drying distillation column 40. NPB, IPB, dibromopropane and water are brought into distillation column 40 through line 34. Water is carried overhead though line 42, passed through heat exchanger 38 and returned to phase separation vessel 30. NPB, IPB, dibromopropane are carried through line 44, through reboiler 46 and into distillation column 50, although a portion can be recirculated to distillation column 40 through line 48 as distillation conditions dictate. Thereafter the scheme is the same as described above for FIG. 1.

Figure 3:
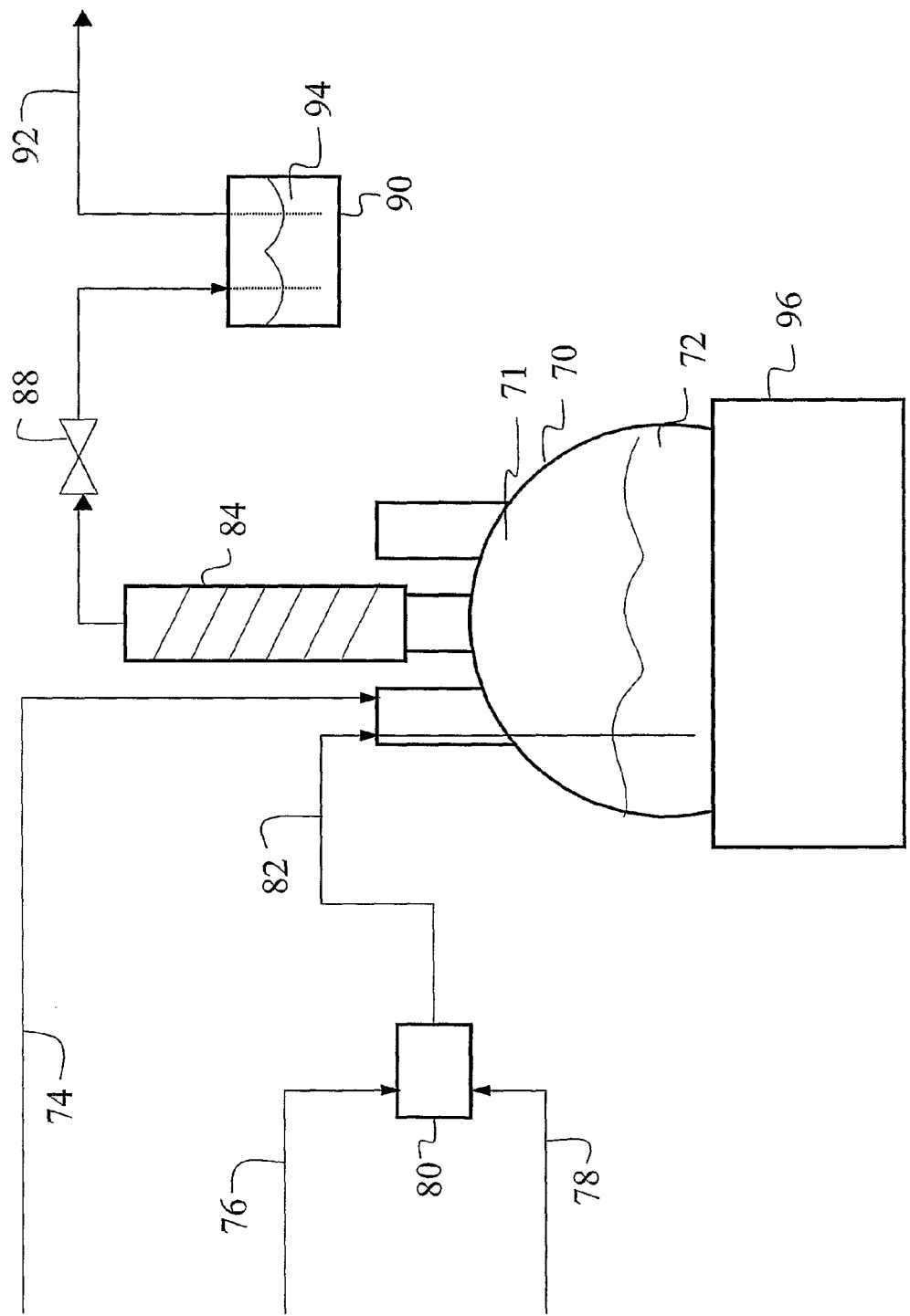
FIG. 3 is a schematic flow diagram of a synthesis portion of a process of this invention on a laboratory scale.

An optional propene hydrobromination reaction system involving pre-mixing propene and oxygen-containing gas is illustrated in FIG. 3. FIG. 3 depicts a laboratory set-up and process scheme for pre-mixing propene and oxygen-containing gas, with propene being fed through line 76 and oxygen-containing gas through line 78 into propene/oxygen-containing gas pre-mixer vessel 80. Care is taken from this point forward to make certain that a propene/oxygen molar ratio is maintained that keeps the mixture rich in propene and outside the upper explosive range for propene and oxygen. The propene/oxygen-containing gas mixture is introduced via line 82 sub-surface into a 60 psi (413.7 kPa) rated 3-necked flask 70 containing a liquid heel 72 of in initial mixture of hydrogen bromide and NPB and head space 71. Additional hydrogen bromide at 40 psi (275.8 kPa) is introduced via line 74 super-surface into flask 70. Reaction temperature in the range of about 20-60° C. is maintained by use of a water bath 96. A 60 psi (413.7 kPa) rated condenser 84 allows only vent gas to be removed through back-pressure regulator 88 so that a desired pressure in the range of about 25 to 60 psi (172.4-413.7 kPa) can be maintained. The composition of this vent gas will be predominately unreacted hydrogen bromide. The vent gas passes through a water scrubber 90, having water content 94. Hydrogen bromide will dissolve in the water. Pressure build-up will be avoided in water scrubber 90 by permitting non-reactive propane, which is an impurity in propene, to exit via line 92. The crude reaction mixture will remain in flask 70 until removed in a suitable manner for subsequent purification procedures.

In a preferred embodiment of the invention, crude reaction mixture comprising at least a mixture of isomers of propyl bromide is washed with a wash of an aqueous solution of 12 wt. % NaOH by mixing the crude reaction mixture with the aqueous NaOH and conducting a phase separation on the organic/aqueous phases formed. Washing and separating procedures are conducted using conventional laboratory equipment such as Erlenmeyer flasks and separatory funnels. The NaOH wash can be repeated one or more times, if desired. A water wash can be performed by mixing water with the crude reactor product before performing the aqueous NaOH wash in order to remove HBr and reduce the amount of NaOH necessary to neutralize substantially all of the HBr. Also, an optional water wash can be performed on the organic phase formed in the aqueous NaOH wash step in order to remove NaOH before conducting the distillation step or steps. The organic phases of these wash steps comprise the NPB-containing feeds for subsequent distillation steps.

Figure 4:
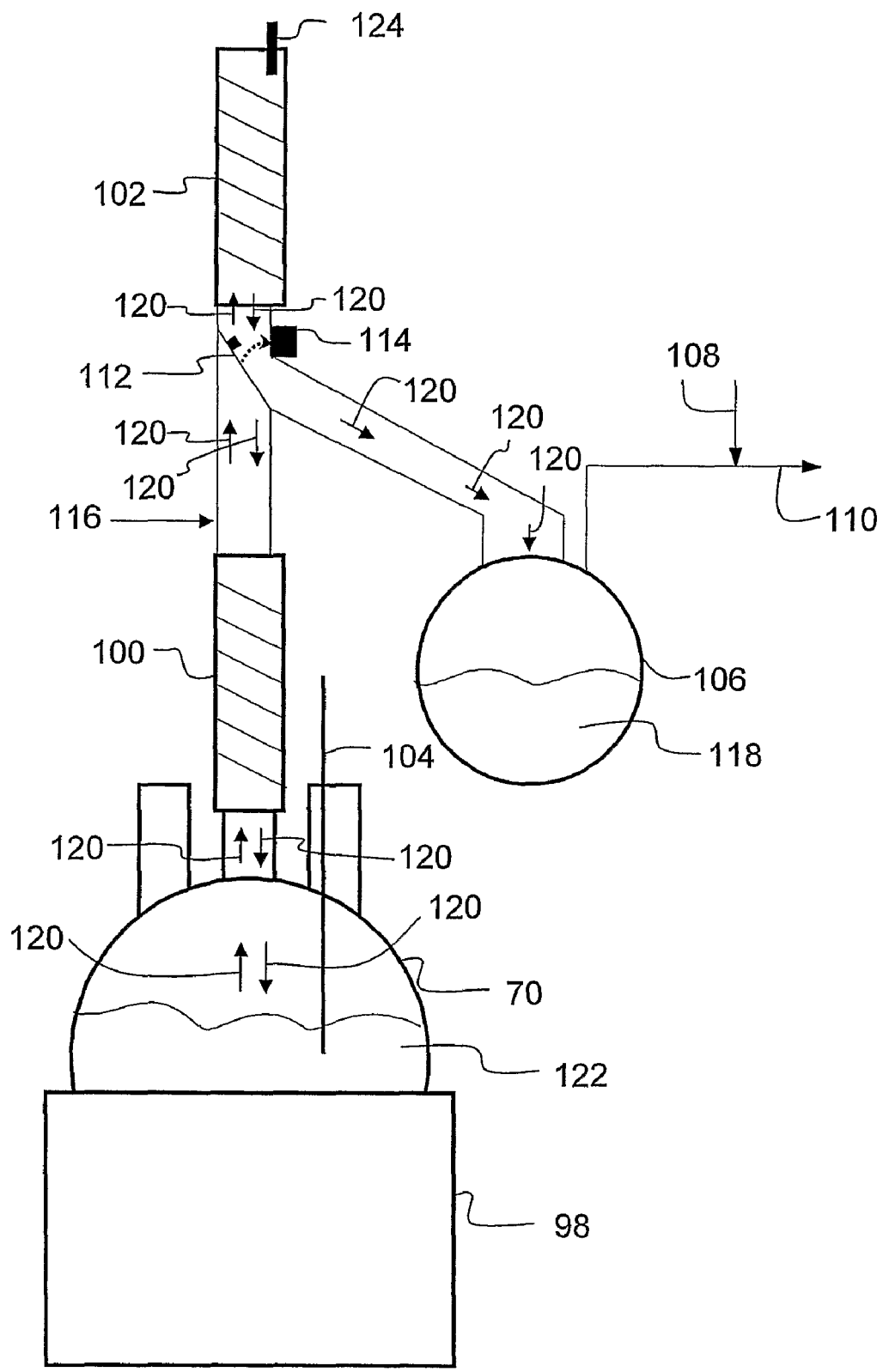
FIG. 4 is a schematic flow diagram of a purification process of this invention on a laboratory scale.

FIG. 4 illustrates a preferred laboratory distillation set-up for a first distillation of the organic phase or phases from prior wash steps. Operation is conducted as a batch process with the organic phase of the wash step being distilled from three-necked flask 70. Heat is supplied by heating mantle 98 with Variac control (not shown). Bottoms temperature range of 72° C. to 73° C. is monitored using thermometer 104. Distillation column 100 is shown with a variable reflux head 116 comprising swinging funnel 112. Electromagnet 114 and a timer (not shown) are used to provide variable reflux ratios in the range of about 3:1 to 10:1 as parts of distillate 120 going up column 100 to parts of distillate 120 allowed to flow into receiver 106 and collected as receiver contents 118. As distillate 120 flows up column 100, it is cooled and condensed in condenser 102 which has a coolant temperature in the range of 5 to 10° C. Condenser temperatures are monitored using thermometer 124. As distillate 120 cools and condenses, it flows back into distillation column 100 or out to receiver 106. The direction of flow of distillate 120 is determined by the position of swinging funnel 112. FIG. 4 depicts swinging funnel 112 in a position which allows distillate 120 to flow into receiver 106 from condenser 102. When electromagnet 114 is activated, swinging funnel 112 moves in the direction of the dashed arrow so as configure the path of flow of distillate 120 back to column 110 to thus provide reflux. The period of time of activation of electromagnet 114 controls the reflux ratio by diverting distillate flow between reflux condition and draw-off condition based on adjustment of a timer (not shown). Atmospheric vent line 110 with nitrogen input line 108 allows venting of vapors as needed from receiver 118. High purity NPB is provided in the bottoms product left in flask 70 at the conclusion of the distillation, while IPB and other impurities are carried into receiver 106.

Column 100 may be of any suitable configuration to perform the necessary separation. A preferred column type is a 30 inch (76.2 cm), 20-tray Oldershaw column. Columns having additional trays are useful for increased efficiency if space permits.

Figure 5:
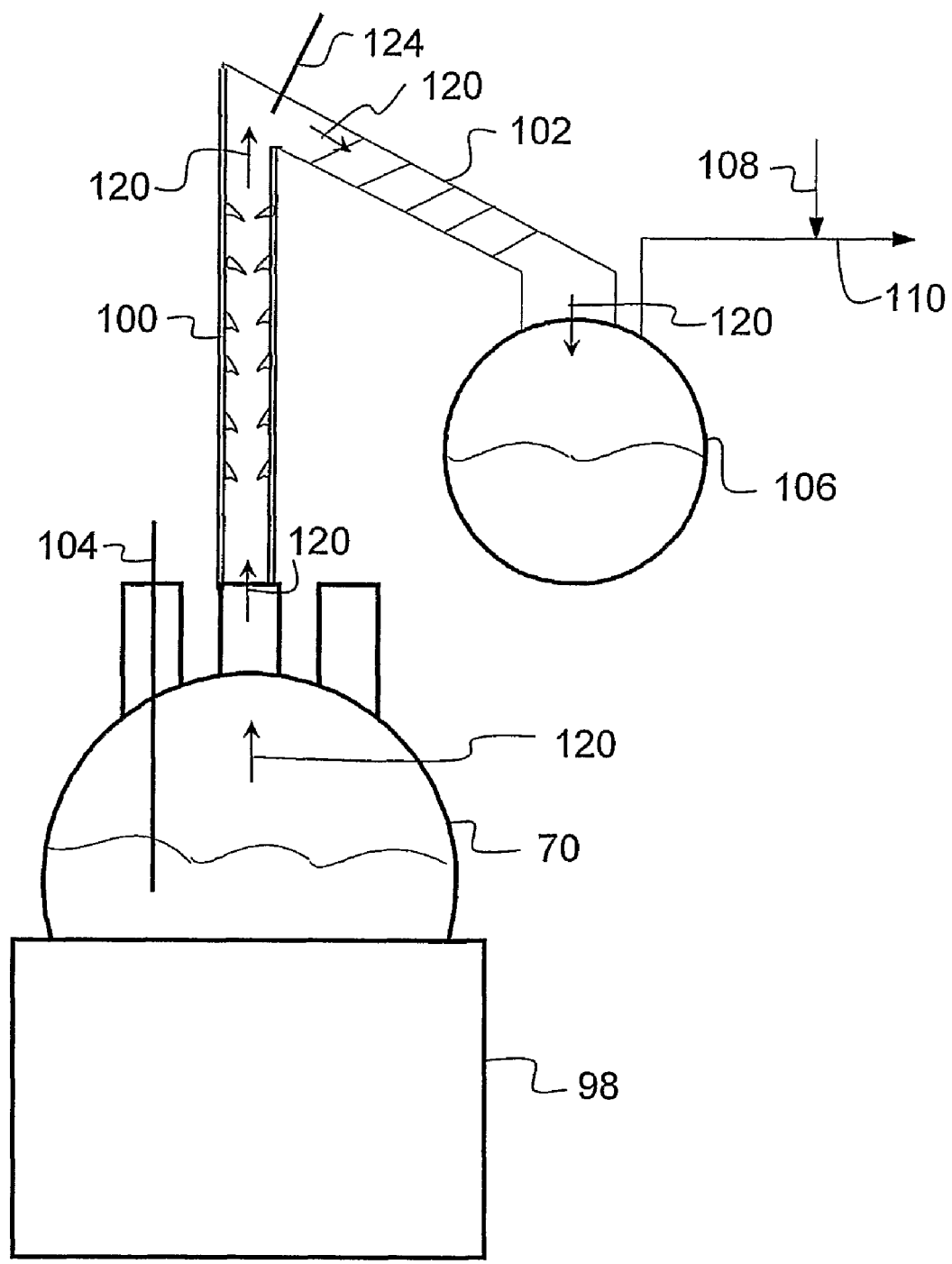
FIG. 5 is a schematic flow diagram of another purification process of this invention on a laboratory scale.

FIG. 5 shows a preferred laboratory equipment set-up for a flash distillation of the bottoms product of the distillation illustrated in FIG. 4. A first distillation bottoms product is placed in a three-necked round-bottomed flask 70, having second distillation column 100 and condenser 102 connected as shown. Heat is supplied by heating mantle 98 with variable Variac control (not shown). Bottoms distillation temperature is targeted for about 70.3° C. at 14.7 psi (101.3 kPa) and overhead distillation temperature progresses up to about 71 to 72° C. at 14.7 (psi (101.3 kPa). Thermometers 104 and 124 monitor bottoms and overhead temperatures, respectively. Distillate 120 is carried up Vigreaux-type column 100, passed though condenser 102 and collected in receiver 106, as very high purity NPB product. Nitrogen input line 108 and vent line 110 are shown which allow periodic venting of vapors from receiver 106 as appropriate.

The following Examples illustrate, but are not intended to limit, this invention.

EXAMPLES

Example 1

Hydrobromination of Propene

A laboratory-scale backpressure reactor was constructed using a heavy-walled, 60 psi (413.7 kPa) rated 500 mL flask with threaded Teflon® polymer coated connections to a 60 psi (413.7 kPa) rated condenser (5° C. coolant) and adapters with the vent gas connected to a back pressure regulator. An initial liquid volume of 178.70 g (1.124 mol) NPB was added into the reactor. Hydrogen bromide gas was fed super-surface, through 0.5 inch (1.27 cm) Teflon® polymer coated tubing increasing a rate of 0.67 g/min. for 3-4 minutes. Propene was fed through 0.25 inch (0.635 cm) PTFE tubing initially at approximately 205 mL/min though calibrated flow meters into a Fischer-Porter bottle. Oxygen-containing gas (air) (6 mL/min) was metered via computerized pump using #14 Viton tubing into the Fischer-Porter bottle. The propene and air mixture was fed subsurface to the 500 mL flask during a 4.5 hour addition, during which HBr feed was maintained at approximately 0.67 gm/min. The hydrobromination was performed at 20-23° C., 30-31 psi (206.8–213.7 kPa) with these pressures being maintained using a back-pressure regulator. The liquid product was condensed as it was formed. The vent gas was scrubbed through water to remove HBr and the exit gas flow was measured intermittently with a gas (Bunte) buret. The calculated conversion to NPB, based on propene feed and hydrogen bromide exit gas amounts was 99.90 mole %. The crude product contained 1.30% dissolved HBr, and after washing with 87.26 g water and phase separation, an isolated yield of 250 g of propyl bromide in excess of the initial heel was obtained. Analysis of the vent gas showed 0.10% propene, 1.90% propane and indicated sufficiently low flow of combustible organics so as to maintain below the flammability range of both propene and propane in air. Propane, an impurity in propene, is the predominant hydrocarbon vent gas under these experimental conditions (with 1-3% excess HBr flow in excess of stoichiometric amount necessary when measured at atmospheric pressure) and is unreactive to that it passes through the system as an inert flammable exit gas. GC analysis of the product indicated 97.80% NPB, 1.57% IPB, 0.20% dibromopropane on a GC area percent basis. Typically, the exit gas analysis had a reaction completion of greater than 99.5%. The reactor yield is limited by the selectivity for NPB, typically 96.0-98.4%.

Example 2

Aqueous Sodium Hydroxide Wash and Water Wash

An embodiment of a process of this invention was conducted on a crude mixture of isomers of propyl bromide containing 95.76 GC area % NPB, 3.91 GC area % IPB and 0.13 GC area % dibromopropane. 350 mL (471.6 g, 2.97 mols) of a crude hydrobromination product, having 95.76% NPB, 3.12% IPB and 0.13% dibromopropane, was washed in a 500 mL Erlenmeyer flask using 160 mL of an aqueous solution of 12% NaOH and phase separated using conventional laboratory equipment. A clean phase separation was obtained within 5-10 seconds to give 451.65 g (95.73%)

yield, including physical losses. GC results were as follows for the crude product after the NaOH wash: 95.86% NPB, 3.81% IPB, 0.15% dibromopropane. The NaOH wash procedure was repeated on a second sample of crude hydrobromination product with similar results. Another water wash was performed on the organic phase thus formed in order to minimize the possibility of carrying NaOH into the distillation train.

Example 3

Oldershaw Distillation

An Oldershaw distillation step was performed on the organic phase from the water wash step of Example 2. Samples from the water wash step in Example 2 were combined and a total of 887.25 g used as feed for the distillation. A 500 mL three-necked round bottomed flask was equipped with a 30 inch, 20-tray Oldershaw column with variable reflux head controlled by an electromagnet and timer for reflux ratio control. Heating was supplied with a 500 mL heating mantle connected to a Variac thermal controller using manual control. The condenser coolant temperature was 5-10° C. The reflux was initially 3:1 and gradually increased to 10:1 with most product collection occurring at 66.0-68.7° C. and bottoms temperature of 72.9-73.0° C. Mass balance for the experiment was 79.45 wt. % and the total distillate comprised 33.54% of feed. Distillate of 89.18 g was collected (30% of total) and analyzed by GC which showed 29.98% IPB, 69.66% NPB. Analysis of the distillate at 67% (of the total distillate collected) gave 6.51% IPB, 93.48% NPB. Upon completion, the bottoms (414.22 g, 43.46% of feed) were analyzed by GC: propene <0.01%, IPB 0.02%, NPB 99.70%, and dibromo-propane 0.24% all reported as GC area percentages. Mass balance across the distillation was 79.5 wt. % including losses due mainly to evaporation and the competing elimination reaction.

Example 4

Flash Distillation

A second, optional, single-stage flash distillation was performed in a single-stage Vigreaux column with attached condenser under nitrogen on the bottoms product of the Oldershaw distillation from Example 3 in order to better separate NPB from remaining color-containing nonvolatiles. Overhead distillation temperature configuration was 71.4° C. at 14.7 psi (101.3 kPa) and bottoms distillation temperature progressed up to 73° C. at 14.7 psi (101.3 kPa). Using a Variac/heating mantle with manual control, 264.09 g distillate was obtained. Over the course of this distillation the APHA color was improved from >100 in the initial feedstock to a color of APHA 10 in the distillate. The center cut (63.75% of feed) was isolated and analyzed as follows: an APHA color of 5-10; NPB content of 99.94%, IPB content of 0.02%, and dibromopropane content of 0.04% (by GC area %). Generally, compositions of this invention have a purity of at least about 99.9% NPB with the balance being IPB, dibromopropane and other, unknown impurities.

Example 5

Thermal Stability Storage Tests at 60° C.

Highly pure, distilled propyl bromide product as provided in Example 4 was separated into portions and thermal storage stability tests were conducted on the portions. Twelve 60 mL samples of NPB were placed in 4 oz. (118 mL) bottles and closed with Teflon® polymer coated lids upon thermal equilibration. All samples, in addition to being closed with Teflon® polymer coated lids were additionally kept in a closed receptacle where the temperature was maintained at 60° C. The bottles used were constructed of glass, although other suitable containers can be used if manufactured from a chemically inert material which does not chemically interact with the sample. At the time intervals indicated in the Table below, samples were retrieved from the sample bottles and then re-closed and returned to the closed receptacle. A sample of an unstabilized mixture of NPB and IPB which is a composition of the present invention is reported as sample 1.

Other samples of propyl bromide from various sources were also subjected to analytical procedures for comparison. A sample of NPB obtained from Aldrich Chemical Co., which was spiked with 50 ppm epoxybutane as a stabilizer is listed as sample A in the Table. NPB from this same Aldrich Chemical Co. source was tested without a stabilizer and reported as Sample B.

| Table of Analytical Results of Thermal Stability Storage Tests | | | | | |
|---|---|---|---|---|---|
| Sample | Time at 60° C. (hours) | APHA color | NPB (GC %) | IPB (GC %) | dibromopropane (GC %) |
| 1[1] | 0 | 5 | 99.94 | 0.02 | 0.04 |
|  | 480 | 10 | 99.90 | 0.03 | 0.06 |
|  | 720 | 5 | 99.79 | 0.03 | 0.06 |
| A[2] | 0 | 5 | 98.93 | 0.63 | 0.01 |
|  | 480 | 15 | 98.91 | 0.64 | 0.01 |
|  | 720 | 5 | 99.03 | 0.58 | 0.01 |
| B[3] | 0 | 5 | 98.91 | 0.65 | 0.01 |
|  | 480 | 10 | 99.11 | 0.54 | 0.01 |
|  | 720 | 15 | 98.84 | 0.63 | 0.01 |

[1] Product of oxygen-initiated hydrobromination of propene 30.7-32.7 psi (211.7-225.5 kPa), 33-35° C.], purified according to embodiment of this invention, per procedures of Examples 2-4.
[2] Aldrich Chemical Co. NPB with stabilizer
[3] Aldrich Chemical Co. NPB without stabilizer As may be seen from the data of the Table, the present invention provides high purity unstabilized IPB product, having excellent APHA color and very low IPB content when maintained under thermal stability test conditions. Although it is common practice to add stabilizers, such as nitro-alkanes, alkenes, 1,3-dioxylane, amines, nitrobenzene, and or an epoxide such as 1,2-epoxybutane, compounds of this invention are composed of the propyl bromides as produced.

Analytical Conditions for Propyl Bromide

Gas chromatography (GC) analyses were performed using a HP-5890 Series II GC with a flame ionization detector and He carrier gas with a split injector and 5 psig (19.7 psi, 135.8 kPa) column head pressure and He flow rate of 150 μL/min, using a 30 meter×0.53 mm DB-624 column with a film thickness of 3.0 um. GC thermal conditions were as follows: Injector 260° C., detector 260° C., Oven initial: 60° C., held 10 minutes, increased at a rate of 10° C./min to a final temperature of 250° C., then held at final temperature for 3 minutes. Samples of crude hydrobromination product were washed with water, dried with 5 Å molecular sieves, and analyzed (0.5 uL) without dilution using GC area percent response for a flame ionization detector. Samples of distilled propyl bromide were analyzed (0.5 uL) by gas chromatography, using these conditions, without dilution of the samples. The retention times were 3.0 minutes and 3.8 minutes for IPB and NPB respectively. In this manner trace levels, down to ca. 20 ppm, of IPB can be detected.

Quantitative analyses of IPB at 0.03 GC area % in the purified products were performed using a five point calibration ($R^2$-0.9959) of the relative GC response for the range 73 ppm-1157 ppm of IPB. Samples were prepared for GC analysis by addition of 300 μL sample into 9.0 mL of a solution comprised of 350 mL chlorobenzene, 300 μL dodecane using the same GC conditions as previously explained.

APHA color was determined with an Orbeco-Hellige "Aqua Tester" using a 22.86 cm (9 inch) (length)×1.27 cm (0.5 inch) (inner diameter) tube with side-by-side comparisons to examples of known APHA color.

The thermal storage stability tests were conducted on 60 mL samples which were placed in 118 mL bottles and closed with Teflon® polymer coated lids upon thermal equilibration. All samples were kept in a Thermodyne mechanical oven where the temperature was maintained at 60° C. At the designated time intervals, samples were retrieved from the sample bottles, analyzed, subjected to a nitrogen pad, then re-closed and returned to the oven.

General Considerations.

Compounds referred to by chemical name or formula anywhere in this document, whether referred to in the singular or plural, are identified as they exist prior to coming into contact with another substance referred to by chemical name or chemical type (e.g., another component or a solvent). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g. "comprises", "is"), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

This invention is susceptible to considerable variation in its practice. Therefore the foregoing description is not intended to limit, and should not be construed as limiting, the invention to the particular exemplifications presented hereinabove.

The invention claimed is:

1. A process of preparing n-propyl bromide in the form of a crude reaction mixture containing at least 95 GC area % n-propyl bromide, which process comprises feeding (A) a molecular oxygen-containing gas, (B) propene as a gas and (C) hydrogen bromide as a gas, either sequentially or concurrently into a liquid phase mixture containing at least n-propyl bromide and hydrogen bromide wherein the hydrogen bromide in the liquid phase mixture initially is present in an amount in the range of 1.1 wt. % to 1.5 wt. % based on the weight of the liquid phase mixture, wherein at least the molecular oxygen-containing gas of (A) and the propene gas of (B) are fed subsurface to the liquid phase mixture, with the provisos that:

i) the molecular oxygen-containing gas and the propene come together in the absence of hydrogen bromide only in a propene:oxygen molar ratio in the range of 145:1 to 180:1, and ii) the process is conducted in reaction equipment having contacting surfaces essentially devoid of reaction inhibitors, and wherein HBr is maintained at a stoichiometric excess, when measured at atmospheric pressure, relative to propene present in the liquid phase mixture during the process.

2. A process according to claim 1 wherein the molecular oxygen-containing gas utilized in the process is air.

3. A process according to claim 1 wherein the feeds of molecular oxygen-containing gas, propene and hydrogen bromide are separate feeds.

4. A process according to claim 1 wherein the feeds of molecular oxygen-containing gas and propene are combined before being fed subsurface to the liquid phase mixture.

5. A process according to claim 1 wherein the reaction inhibitors are one or more metals or one or more metal-containing compounds.

6. A process according to claim 5 wherein the one or more metals is iron or titanium.

7. A process according to claim 5 wherein the one or more metal-containing compounds contains iron or titanium.

8. A process according to claim 1 for separating n-propyl bromide from the crude reaction mixture which process further comprises:

(I) washing at least a portion of the crude reaction mixture one or more times with a wash comprising an aqueous solution or aqueous suspension of at least one alkali metal hydroxide having a molar concentration in the range of 3 to 5 moles per liter, to form an aqueous phase and an organic phase, and then separating the phases thus formed;

(II) optionally, washing at least a portion of the organic phase from (I) with water to form an aqueous phase and an organic phase and then separating the phases thus formed;

(III) either
  (A) when (I) is conducted and (II) is not conducted, distilling at least a portion of the organic phase from (I) one or more times; or
  (B) when (I) and (II) are conducted, distilling at least a portion of the organic phase from (II) one or more times; and (IV) forming a propyl bromide product mixture wherein the propyl bromide product mixture is comprised of at least 99.7 GC area % n-propyl bromide and no more than 0.05 GC area % isopropyl bromide.

9. A process according to claim 8 further comprising washing at least a portion of the crude reaction mixture with water under conditions such that an aqueous phase and an organic phase are formed, separating the phases thus formed and then continuing with step (I) on the organic phase thus formed.

10. A process according to claim 8 wherein the propyl bromide product comprises at least 99.8 GC area % n-propyl bromide and no more than 0.03 GC area % isopropyl bromide.

11. A process according to claim 8 wherein the wash of aqueous solution or aqueous suspension of alkali metal hydroxide has a molar concentration in the range of 3.2 to 4.5 moles per liter.

12. A process according to claim 8 wherein the alkali metal hydroxide utilized in the process is NaOH.

13. A process according to claim 8 further comprising drying the organic phase from (I) or (II) before distillation.

14. A process according to claim 13 wherein drying takes place by contacting at least a portion of the organic phase from (I) or (II) with a drying agent and separating a dried organic phase before distillation.

15. A process according to claim 14 wherein the drying agent utilized in the process is either calcium sulfate or calcium chloride.

16. A process according to claim 8 wherein, when (I) is conducted and (II) is not conducted, at least a portion of the organic phase from (I) is distilled at least three times.

17. A process according to claim 8 wherein the product mixture, if subjected to storage in a closed chemically inert container at 60° C. for at least 480 hours, has an APHA color of 10 or less, and wherein the product mixture is devoid of any added stabilizer component.

18. A process of preparing n-propyl bromide in the form of a crude reaction mixture containing at least 95 GC area % n-propyl bromide, which process comprises feeding (A) a molecular oxygen-containing gas, (B) propene as a gas and (C) hydrogen bromide as a gas, either sequentially or concurrently into a liquid phase mixture containing at least n-propyl bromide and hydrogen bromide wherein the hydrogen bromide in the liquid phase mixture initially is present in an amount in the range of 1.1 wt. % to 1.5 wt. % based on the weight of the liquid phase mixture, wherein at least the molecular oxygen-containing gas of (A) and the propene gas of (B) are fed subsurface to the liquid phase mixture, with the provisos that:
  i) the molecular oxygen-containing gas and the propene do not come together in the absence of hydrogen bromide, and
  ii) the process is conducted in reaction equipment having contacting surfaces essentially devoid of reaction inhibitors,
and wherein HBr is maintained at a stoichiometric excess, when measured at atmospheric pressure, relative to propene present in the liquid phase mixture during the process.

19. A process according to claim 18 wherein the molecular oxygen-containing gas utilized in the process is air.

20. A process according to claim 18 wherein the feeds of molecular oxygen-containing gas, propene and hydrogen bromide are separate feeds.

* * * * *